US012055552B2

United States Patent
Chen et al.

(10) Patent No.: US 12,055,552 B2
(45) Date of Patent: Aug. 6, 2024

(54) METHOD FOR DIAGNOSIS BASED ON CIRCULATING EXTRACELLULAR VESICLES

(71) Applicant: WellSIM Biomedical Technologies, Inc., San Jose, CA (US)

(72) Inventors: Yuchao Chen, Rodeo, CA (US); Katherine Tuchez, San Jose, CA (US)

(73) Assignee: WELLSIM BIOMEDICAL TECHNOLOGIES, INC., San Jose, CA (US)

( * ) Notice: Subject to any disclaimer, the term of this patent is extended or adjusted under 35 U.S.C. 154(b) by 0 days.

(21) Appl. No.: 17/947,168

(22) Filed: Sep. 18, 2022

(65) Prior Publication Data

US 2023/0266341 A1 Aug. 24, 2023

Related U.S. Application Data

(60) Provisional application No. 63/339,446, filed on May 7, 2022, provisional application No. 63/312,034, filed on Feb. 20, 2022.

(51) Int. Cl.
G01N 33/543 (2006.01)
G01N 33/50 (2006.01)
G01N 33/68 (2006.01)

(52) U.S. Cl.
CPC ... *G01N 33/6896* (2013.01); *G01N 33/54306* (2013.01); *G01N 33/54393* (2013.01); *G01N 2333/70596* (2013.01); *G01N 2800/2821* (2013.01)

(58) Field of Classification Search
CPC ......... G01N 33/6896; G01N 33/54306; G01N 33/54393; G01N 2333/70596; G01N 2800/2821
See application file for complete search history.

(56) References Cited

U.S. PATENT DOCUMENTS

2018/0217165 A1* 8/2018 Goetzl ............... G01N 33/6896
2021/0325409 A1* 10/2021 Braudeau ............... G06N 20/00

FOREIGN PATENT DOCUMENTS

WO WO2004/017816 A2 * 3/2004
WO WO-2020086751 A1 * 4/2020 ......... C12N 15/1065

OTHER PUBLICATIONS

Applied Microarray, print retrieved Feb. 2023, (https://appliedmicroarrays.com/product/nexterion-16-well-coated-and-uncoated-slides/) (Year: 2023).*

(Continued)

*Primary Examiner* — Shafiqul Haq
*Assistant Examiner* — Nam P Nguyen
(74) *Attorney, Agent, or Firm* — Jun He Law Offices P.C; Yi Zhang

(57) ABSTRACT

The present disclosure provides a method for diagnosis based on proteins present on the surface of circulating extracellular vesicles. The method comprises incubating a sample of the subject with a detection antibody linked to a detectable label, contacting the sample with a capture antibody immobilized on a substrate, and detecting the detectable label on the circulating EV immobilized on the substrate. Compared to the method currently known in the art, the method disclosed herein has the advantages of high sensitivity with low cost and rapid procedure, high specificity.

12 Claims, 8 Drawing Sheets

(56) References Cited

OTHER PUBLICATIONS

Baek et al. ("Multiplexed Phenotyping of Small Extracellular Vesicles Using Protein Microarray (EV Array)" Exosomes and Microvesicles; Methods in Molecular Biology, vol. 1545, pp. 117-127, Chapter 8, published Dec. 10, 2016). (Year: 2016).*

Jakobsen et al. ("Exosomal proteins as potential diagnostic markers in advanced non-small cell lung carcinoma", Journal of Extracellular Vesicles, 2015, vol. 4, 26659, pp. 1-10, published Mar. 2, 2015). (Year: 2015).*

Odaka et al. ("Platelet-derived extracellular vesicles are increased in sera of Alzheimer's disease patients, as revealed by Tim4-based assays," FEBS Open Bio, vol. 11, pp. 741-752, published Dec. 20, 2020) (Year: 2020).*

Pablo et al. ("Protein Microarrays in Neurodegenerative Diseases," Current Proteomic Approaches Applied to Brain Function, Neuromethods book series, chapter 4, vol. 127, pp. 43-62, published Jun. 28, 2017). (Year: 2017).*

Picciolini et al. ("Detection and Characterization of Different Brain-Derived Subpopulations of Plasma Exosomes by Surface Plasmon Resonance Imaging," Analytical Chemistry, vol. 90, pp. 8873-8880, published Jul. 4, 2018). (Year: 2018).*

Cheung et al., "Rapid Detection and Trapping of Extracellular Vesicles by Electrokinetic Concentration for Liquid Biopsy on Chip", Micromachines, vol. 9 (306), pp. 1-12, published Jun. 19, 2018. (Year: 2018).*

Kayoung Kim et al., "Clinically accurate diagnosis of Alzheimer's disease via multiplexed sensing of core biomarkers in human plasma", Nat Commun, Jan. 8, 2020;11(1):119.

Longfei Jia et al., "Concordance between the assessment of AB42, T-tau, and P-T181-tau in peripheral blood neuronal-derived exosomes and cerebrospinal fluid", Alzheimers Dement, Aug. 2019; 15(8):1071-1080.

Chothia, C. et al., "Domian Association in Immunoglobulin Molecules The Packing of Variable Domains", J Mol Biol 186(3):651-63 (1985).

Chothia, C. et al., "Conformations of immunoglobulin hypervariable regions", Nature 342 (6252):877-83 (1989).

Al-Lazikani, B. et al., "Standard Conformations for the Canonical Structures of Immunoglobulins", J Mol Biol 273 (4):927-48 (1997).

* cited by examiner

METHOD FOR DIAGNOSIS BASED ON CIRCULATING EXTRACELLULAR VESICLES

CROSS-REFERENCE TO RELATED APPLICATIONS

This application claims the priority of U.S. provisional application No. 63/312,034, filed Feb. 20, 2022, and 63/339,446, filed May 7, 2022, the entire disclosure of which are incorporated herein by reference.

FIELD OF THE INVENTION

The present invention generally relates to diagnosis and therapeutics. More particularly, the invention relates to a method for detecting disease related antigens present on the surface of extracellular vesicles.

BACKGROUND OF THE INVENTION

Extracellular vesicles (EVs) are cell-derived vesicles that are present in many eukaryotic fluids including blood, urine, cerebrospinal fluid, lavage, and cultured medium of cell culture. EVs play a key role in processes such as coagulation, intercellular signaling, and waste management. There is a growing interest in the therapeutic and diagnostic applications of EVs as they are found to participate in the progression of many diseases. For example, EVs are actively released from tumor cells that have shown to contain surface or molecular cargo biomarkers that include tumor-specific proteins, -small molecules, -nucleic acids (mRNA, microRNA, and DNA) that are indicative of the cancer progression and the stage.

In another example, neuron-derived EVs are considered a significant mediator in regulating AD pathogenesis and are involved in AD propagation. For example, EVs play critical roles in propagating tau pathology by spreading the disease-causing misfolded protein tau throughout the brain. As a result, molecules carried by EVs, including proteins, nucleic acids, and lipids, provide a rich source for profiling AD-associated biomarkers. Moreover, EVs can pass through the blood-brain barrier into the peripheral circulation, enabling interrogation of blood-based AD biomarkers in a less invasive manner. Studies have revealed that circulating EVs in plasma carry substantial amounts of AD biomarkers, such as t-tau (100-500 pg/ml), p-tau181 (50-200 pg/ml), and Aβ42 (2-30 pg/ml), which were observed elevated in AD patients up to 10 years prior to clinical onset.

Currently, EVs are used to detect diseases in combination with various technologies, including mass spectrometry or complicated electrical/optical sensor based on nano/microfabrication. These methods, however, have several limitations, such as time consuming, tedious workflow and/or high cost. Therefore, there is a continuing need to develop methods for diagnosis that are less expensive, easy to operate, highly sensitive and specific, and highly scalable.

BRIEF SUMMARY OF THE INVENTION

In one aspect, the present disclosure provides a method for detecting disease-associated proteins present on the surface of circulating extracellular vesicles (EVs). In one embodiment, the method includes incubating the circulating EVs with a detection antibody linked to a detectable label, wherein the detection antibody specifically binds to a disease-specific antigen present on the surface of the circulating EV. The method further includes contacting the circulating EVs with a capture antibody immobilized on a substrate, wherein the capture antibody specifically binds to a surface antigen of the circulating EV, thus immobilizing the circulating EV on the substrate; and detecting the detectable label on the circulating EV immobilized on the substrate.

It is understood that the steps described above or in any embodiment disclosed herein can be performed in any order operably possible. For example, in another embodiment, the incubating step in the method is performed after the contacting step. In such case, the method comprises contacting the circulating EVs with a capture antibody immobilized on a substrate, wherein the capture antibody specifically binds to a surface antigen of the circulating EV, thus immobilizing the circulating EV on the substrate; then incubating the immobilized circulating EVs with a detection antibody linked to a detectable label, wherein the detection antibody specifically binds to a disease-specific antigen present on the surface of the circulating EV; and detecting the detectable label on the circulating EV immobilized on the substrate.

In some embodiments, the surface antigen recognized by the capture antibody is selected from the group consisting of CD9 (also known as: BTCC-1, DRAP-27, MIC3, MRP-1, TSPAN-29 or TSPAN29; NCBI Gene ID: 928), CD18 (also known as: ITGB2, LAD, LCAMB, LFA-1, MAC-1, MF17 or MFI7; NCBI Gene ID: 3689), CD63 (also known as: LAMP-3, ME491, MLA1, OMA81H or TSPAN30; NCBI Gene ID: 967), CD81 (also known as: CVID6, S5.7, TAPA1 or TSPAN28; NCBI Gene ID: 975), CD56 (also known as NCAM1, MSK39 or NCAM; NCBI Gene ID: 4684) and CD171 (also known as L1 CAM, CAML1, HSAS, HSAS1, MASA, MICS, N-CAM-L1, N-CAML1, NCAM-L1, S10 or SPG1; NCBI Gene ID: 3897). In some embodiments, the EV is derived from a neuron and the surface antigen is CD56 or CD171.

In some embodiments, the substrate is a glass slide. In some embodiments, the glass slide is coated with epoxy. In some embodiments, the capture antibody is immobilized on the glass slide by micro-spotting.

In some embodiments, the detectable label is a fluorophore or a fluorescent microsphere. In some embodiments, the detectable label is detected through a laser-induced confocal fluorescence scanner or a fluorescence microscope.

In some embodiments, the method comprises normalizing the abundance of disease-associated antigen on the circulating EV with the abundance of a control antigen present on the circulating EV. In one embodiment, the method further comprises: incubating the circulating EV with a control antibody linked to a second detectable label, wherein the control antibody specifically binds to a control antigen present on the surface of the circulating EV; and detecting the second detectable label on the circulating EV immobilized on the substrate. In some embodiments, the method further comprises normalizing the abundance of the detectable label on the circulating EV immobilized on the substrate with the abundance of the second detectable label on the circulating EV immobilized on the substrate. In some embodiments, the control antigen is selected from the group consisting of CD9, CD63 and CD81.

In some embodiments, the method for detecting disease-associated proteins present on the surface of circulating EVs can be used for diagnosis. In some embodiments, the method comprises: incubating a sample of the subject with a detection antibody linked to a detectable label, wherein the sample comprises a circulating extracellular vesicle (EV), wherein the detection antibody specifically binds to a disease-specific antigen present on the surface of the circulating EV; contacting the sample with a capture antibody immobilized on a substrate, wherein the capture antibody specifically binds to a surface antigen of the circulating EV, thus immobilizing the circulating EV on the substrate; and detecting the detectable label on the circulating EV immobilized on the substrate, wherein the presence or abundance of the detectable label indicates a likelihood of the disease in the subject.

In some embodiments, the disease is Alzheimer's disease (AD). In some embodiments, the disease-specific antigen is selected from the group consisting of t-tau, p-tau181, p-tau217, Aβ40, and Aβ42.

In some embodiments, the sample is plasma.

In some embodiments, the diagnosis method is based on the detection of multiple disease-specific antigens. In one embodiment, the method comprises: incubating a sample of the subject with a first detection antibody linked to a first detectable label and a second detection antibody linked to a second detectable label, wherein the sample comprises a circulating extracellular vesicle (EV), wherein the first detection antibody and the second detection antibody specifically bind to a first disease-specific antigen and a second disease-specific antigen present on the surface of the circulating EV respectively; contacting the sample with a capture antibody immobilized on a substrate, wherein the capture antibody specifically binds to a surface antigen of the circulating EV, thus immobilizing the circulating EV on the substrate; and detecting the first detectable label and the second detectable label on the circulating EV immobilized on the substrate, wherein the presence or abundance of the first detectable label and the second detectable label indicates a likelihood of the disease in the subject.

In some embodiments, the method further comprises: calculating a ratio of the abundance of the first detectable label to the second detectable label on the circulating EV immobilized on the substrate; and generating a risk score based on the ratio. The risk score can be generated by the method known in the art (see, e.g., Kim K, Kim M J, Kim D W, Kim S Y, Park S, Park C B. Clinically accurate diagnosis of Alzheimer's disease via multiplexed sensing of core biomarkers in human plasma. Nat Commun. 2020 Jan. 8; 11(1):119. doi: 10.1038/s41467-019-13901-z. PMID: 31913282; PMCID: PMC6949261; Jia L, Qiu Q, Zhang H, Chu L, Du Y, Zhang J, Zhou C, Liang F, Shi S, Wang S, Qin W, Wang Q, Li F, Wang Q, Li Y, Shen L, Wei Y, Jia J. Concordance between the assessment of Aβ42, T-tau, and P-T181-tau in peripheral blood neuronal-derived exosomes and cerebrospinal fluid. Alzheimers Dement. 2019 August; 15(8):1071-1080. doi: 10.1016/j.jalz.2019.05.002. PMID: 31422798).

In some embodiments, the abundance of the first and the second detectable labels is normalized with abundance of a control antigen present on the surface of the circulating EV. In some embodiments, the abundance of the control antigen is obtained through detection of a third detectable label linked to a control antibody, wherein the control antibody specifically binds to the control antigen. In some embodiments, the control antigen is CD9.

In some embodiments, the disease is Alzheimer's disease (AD). In some embodiments, the first and the second disease-specific antigens are selected respectively from the group consisting of t-tau, p-tau181, p-tau217, Aβ40, and Aβ42.

In some embodiments, the ratio is selected from the group consisting of ratio of p-Tau181 to t-Tau, ratio of p-Tau181 to Aβ40, ratio of A1342 to Aβ40, ratio of A1342 to t-Tau, ratio of p-Tau217 to t-Tau, and ratio of p-Tau217 to Aβ40.

In some embodiments, the method further comprises calculating risk score from the sum of each ratio multiplied with their coefficients.

In some embodiments, the method comprises determination of the coefficients by using a machine learning algorithm to study a training data set. In some embodiments, the machine learning algorithm is support vector machine (SVM).

In another aspect, the present disclosure provides a method for treating disease in a subject. In some embodiments, the method comprises administering to the subject a therapeutically effective amount of a drug useful for treating the disease, wherein the subject has been determined to have the disease by the diagnosing method disclosed herein. In some embodiments, the method comprises: i) diagnosis-incubating a sample of the subject with a detection antibody linked to a detectable label, wherein the sample comprises a circulating extracellular vesicle (EV), wherein the detection antibody specifically binds to a disease-specific antigen present on the surface of the circulating EV; contacting the sample with a capture antibody immobilized on a substrate, wherein the capture antibody specifically binds to a surface antigen of the circulating EV, thus immobilizing the circulating EV on the substrate; and detecting the detectable label on the circulating EV immobilized on the substrate, wherein the presence or abundance of the detectable label indicates a likelihood of the disease in the subject; ii) treatment; such as, administering to the subject a therapeutically effective amount of a drug useful for treating the disease, wherein the subject has been determined to have the disease by the diagnosing method disclosed herein.

In some embodiments, the disease is Alzheimer's disease (AD). In some embodiments, the drug that can be used in treating AD includes, without limitation: antibodies targeting Aβ (such as Aduhelm), neuroprotective agents (such as ApoE2, Trem2, MT1G, or combinations thereof), hematopoietic stem progenitor cells expressing at least one neuroprotective agent (such as ApoE2, Trem2 or a metallothionein), antibody complex (such as antibody complex modified by a targeted functional molecule), drugs (such as polysaccharide) that inhibit the aggregation of AD-related proteins, like Aβ 42, compounds that degrade AD-related proteins, like microtubule-associated protein tau, NMDA receptor antagonists (such as Memantine), Acetylcholinesterase inhibitor (AChEI) (such as Tacrine, Donepezil, Galanthamine or Rivastigmine).

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE INVENTION

Figure 1:
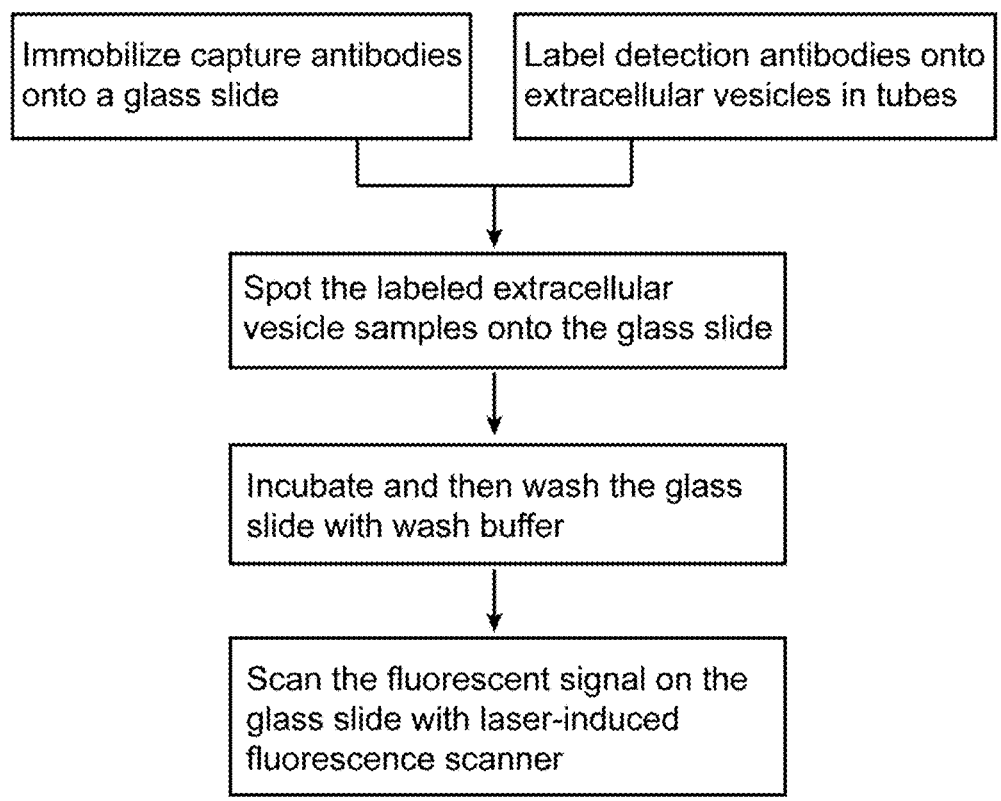
FIG. 1 shows the flow chart of a method of detecting an EV surface protein using a high throughput multiplex immunofluorescent assay according to an embodiment of the invention.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without there specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

DEFINITION

The following definitions are used in the disclosure:

It is understood that as used herein and in the appended claims, the singular forms "a," "an," and "the" include the plural reference unless the context clearly dictates otherwise. Thus, for example, a reference to a "detection antibody" is a reference to one or more detection antibodies, and includes equivalents thereof known to those skilled in the art and so forth.

The term "comprise" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

As used herein, an "antibody" encompasses naturally occurring immunoglobulins as well as non-naturally occurring immunoglobulins, including, for example, single chain antibodies, chimeric antibodies (e.g., humanized murine antibodies), and heteroconjugate antibodies (e.g., bispecific antibodies). Fragments of antibodies include those that bind antigen, (e.g., Fab', F(ab')2, Fab, Fv, and rIgG). See also, e.g., Pierce Catalog and Handbook, 1994-1995 (Pierce Chemical Co., Rockford, Ill.); Kuby, J., Immunology, 3rd Ed., W.H. Freeman & Co., New York (1998). The term antibody also includes bivalent or bispecific molecules, diabodies, triabodies, and tetrabodies. The term "antibody" further includes both polyclonal and monoclonal antibodies.

The term "antibody" as used herein includes any immunoglobulin, monoclonal antibody, polyclonal antibody, multi-specific antibody, or bispecific (bivalent) antibody that binds to a specific antigen (or multiple antigens). A native intact antibody comprises two heavy chains and two light chains. Each heavy chain consists of a variable region (VH) and a first, second, and third constant region (CH1, CH2, CH3), while each light chain consists of a variable region (VL) and a constant region (CL). Mammalian heavy chains are classified as α, δ, ε, γ, and μ, and mammalian light chains are classified as λ or κ. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding, and are often referred to as Fv (for variable fragment) or Fv fragment. The variable regions in both chains generally contains three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Chothia, Kabat, or Al-Lazikani (Chothia, C. et al., J Mol Biol 186(3):651-63 (1985); Chothia, C. and Lesk, A. M., J Mol Biol, 196:901 (1987); Chothia, C. et al., Nature 342 (6252):877-83 (1989); Kabat E. A. et al., National Institutes of Health, Bethesda, Md. (1991); Al-Lazikani, B., Chothia, C., Lesk, A. M., J Mol Biol 273(4):927 (1997)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of $\alpha$, $\delta$, $\epsilon$, $\gamma$, and $\mu$ heavy chains, respectively. Several of the major antibody classes are divided into subclasses such as IgG1 ($\gamma$1 heavy chain), IgG2 ($\gamma$2 heavy chain), IgG3 ($\gamma$3 heavy chain), IgG4 ($\gamma$4 heavy chain), IgA1 ($\alpha$1 heavy chain), or IgA2 ($\alpha$2 heavy chain) in human, and IgG1 ($\gamma$1 heavy chain), IgG2a ($\gamma$2a heavy chain), IgG2b ($\gamma$2b heavy chain), and IgG3 ($\gamma$3 heavy chain) in mouse.

The term "antigen" refers to a substrate capable of inducing adaptive immune responses. Specifically, an antigen is a substance specifically bound by antibodies or T lymphocyte antigen receptors. Antigens are usually proteins and polysaccharides, less frequently also lipids. Suitable antigens include without limitation parts of bacteria (coats, capsules, cell walls, flagella, fimbria, and toxins), viruses, and other microorganisms. Antigens also include tumor antigens, e.g., antigens generated by mutations in tumors. As used herein, antigens also include immunogens and haptens.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. In some embodiments, the antibody that specifically binds to the antigen has a dissociation constant (Kd) of $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g., from $10^{-8}$ M to $10^{-13}$ M, e.g., from $10^{-9}$ M to $10^{-13}$ M).

"Alzheimer's disease (AD) biomarkers", as used herein, refer to any biological molecule (found either in blood, other body fluids, or tissues) that is a sign of an AD-related condition or disease.

As used herein, the term "extracellular vesicle (EV)" encompasses a number of different membrane vesicles produced by cells, the name of which include, for example, micorvesicles, epididimosomes, archeosomes, oncosomes, and exersornessctosomes, microparticles, pro mininosomes, prostasomes, dexosomes, texosomes, archeosomes, oncosomes, and exersornesectosomes, microparticles and shedding microvesicles. Extracellular vesicles (EV) circulate through body fluids, including blood, plasma, serum and urine. Circulating EV may contain exosomes and microvesicles (MV).

The term "sample" as used herein refers to any sample having or suspect of having the target nucleic acid, including sample of biological tissue or fluid origin, obtained, reached, or collected in vivo or in situ. Exemplary biological samples include but are not limited to cell lysate, a cell culture, a cell line, a tissue, an organ, a biological fluid, and the like. In certain embodiments, the sample is a solid sample. In some embodiments, the sample is a tissue.

The term "substrate" refers to a mechanical support upon which material may be disposed to provide functionality, whether mechanical, biological, optical, chemical or other functionality. A substrate may be unpatterned or patterned, partitioned or unpartitioned. Molecules on a substrate may be disposed in features or may be uniformly disposed on the substrate surface.

As used herein, the term "subject" refers to a human or any non-human animal (e.g., mouse, rat, rabbit, dog, cat, cattle, swine, sheep, horse or primate). A human includes pre and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

As used herein, the term "therapeutically effective amount" means the amount of agent that is sufficient to prevent, treat, reduce and/or ameliorate the symptoms and/or underlying causes of any disorder or disease, or the amount of an agent sufficient to produce a desired effect on a cell. In one embodiment, a "therapeutically effective amount" is an amount sufficient to reduce or eliminate a symptom of a disease. In another embodiment, a therapeutically effective amount is an amount sufficient to overcome the disease itself.

The term "treatment," "treat," or "treating" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In some embodiments, treating is preventing. In some embodiments, treating does not include preventing. "Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

Method of Diagnosis

The current method relates to EV-based immunoassay, which implements a pair of antibodies (i.e., capture antibody and detection antibody) to target two specific antigens on EVs. Once non-specific binding is eliminated (validate by isotype control), signals of detectable labels could be detected only when a particle or molecular has specific conjugation with both antibodies, which could significantly reduce noise signal from cross-reaction with various plasma proteins, allowing for high detection specificity even without EV purification. The present disclosure in one aspect provides a method for diagnosing a disease in a subject. This technology has a high resolution that can detect single EVs. With this method, a prediction model with a composite biomarker panel is developed and validated for diagnosis of diseases, e.g., Alzheimer's disease (AD). Comparing to the method currently known in the art, the method disclosed herein has the advantages of high sensitivity with low cost and rapid procedure, high specificity.

In some embodiments, the present invention combines immunological methods (antigen antibody specific binding) with fluorescent labeling technology and developed a high-sensitivity immunofluorescence assay for detection and quantification of biomarkers from plasma EVs, named EXODOTS, with high sensitivity and specificity, high speed, and low cost.

In one embodiment, the method includes incubating the circulating EVs with a detection antibody linked to a detectable label, wherein the detection antibody specifically binds to a disease-specific antigen present on the surface of the circulating EV. The method further includes contacting the circulating EVs with a capture antibody immobilized on a substrate, wherein the capture antibody specifically binds to a surface antigen of the circulating EV, thus immobilizing the circulating EV on the substrate; and detecting the detectable label on the circulating EV immobilized on the substrate.

An exemplary embodiment of the method for diagnosing a disease in a subject described herein is illustrated in FIG. 1. Referring to FIG. 1, a capture antibody is immobilized onto a glass slide. In some embodiments, the capture antibody is immobilized on the glass slide by micro-spotting. Simultaneously or sequentially, a detection antibody is labelled onto EVs comprised in a sample. After that, the sample is spotted onto the locations immobilized with the capture antibody on the substrate. The sample and the capture antibody immobilized on the glass slide are then incubated under specific conditions. After incubation, the glass slide is washed with wash buffer to remove unconjugated EVs, capture antibodies and detection antibodies. Then the glass slide is scanned for signals. For example, referring to FIG. 1, the glass slide is scanned for fluorescent signal with laser-induced fluorescence scanner. By integrating slide-based immunofluorescence assay with a highly sensitive laser-induced confocal fluorescence scanner, the method can achieve single EV resolution with significantly lower cost for consumables (<$10) as well as rapid and simple workflow (<3 hours) without EV pre-purification.

Figure 2A:
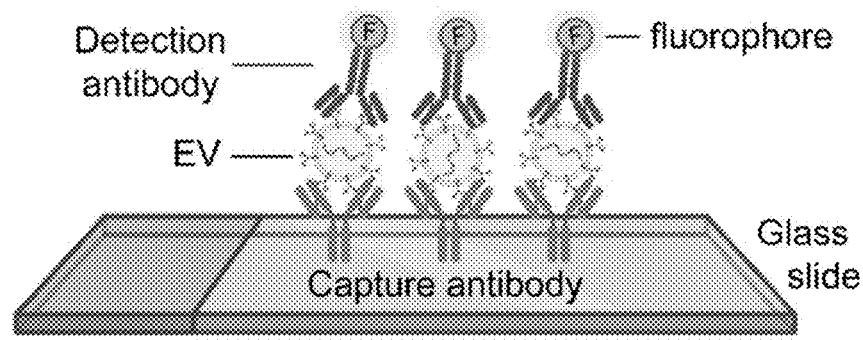
FIG. 2A shows the schematic of detecting biomarkers present of the surface of EV.

FIG. 2A illustrates the structure formed by the detection antibody, the EV and the capture antibody on the glass slide after incubation. It is understood that for the purpose of labelling the disease-specific antigen, the detectable label can be linked to any position on the detection antibody, provided that it does not affect the binding of the detection antibody to the disease-specific antigen. In some embodiments, the detectable labels can be linked to the N terminal of the detection antibody. In some embodiments, the detectable labels can be linked to the C terminal of the detection antibody.

As an example, referring to FIG. 2A, the fluorophore is linked to C terminal of the detection antibody. It can be understood that for the purpose of capturing the EVs through a surface antigen onto the glass slide, the capture antibody can be any forms of antibody with antigen-binding site that is capable of specifically binding to the surface antigen on the EV, such as a full-length antibody, a single chain antibody, etc. As illustrated in FIG. 2A, in one embodiment, the capture antibody is a full-length antibody. It can also be understood that for the purpose of labelling the fluorophore to the disease specific antigen, the detection antibody can be any form of antibody that is capable of specifically binding with the disease-specific antigen on the EVs, such as full-length antibodies, a single chain antibody, etc.

Antigens commonly present on the surface of circulating EVs are known in the art, such as CD9, CD18, CD63, CD81, CD56 and CD171. In some embodiments, the circulating EV is derived from a neuron, and the surface antigen of the circulating EV is CD56 or CD171. Besides, the surface antigen of the circulating EV can be detected to verify the effectiveness of the method. For example, the surface antigen can be used as a control antigen. Specially, the sample can be further incubated with a control antibody linked to a second detectable label, wherein the control antibody specifically binds to the control antigen. In some embodiments, the control antigen is CD9. In some embodiments, the sample can be incubated with the detection antibody and the control antibody simultaneously. Following detection of the second detectable label on the circulating EV immobilized on the substrate, the abundance of the second detectable label on the circulating EV immobilized on the substrate can be used to normalize the abundance of the detectable label linking to the detection antibody on the circulating EV immobilized on the substrate, to reduce sample-to-sample variations and operation variations. It is understood that the control antibody and the capture antibody specifically bind to different surface antigens. Once non-specific binding is eliminated (validate by isotype control), fluorescent signal could be detected only when a particle or molecular has specific conjugation with both antibodies, which could significantly reduce noise signal from cross-reaction with various plasma proteins, allowing for high detection specificity even without EV purification. In some embodiments, the control antibody is an anti-CD9 antibody, and the capture antibody is an anti-CD56 antibody.

Figure 2B:
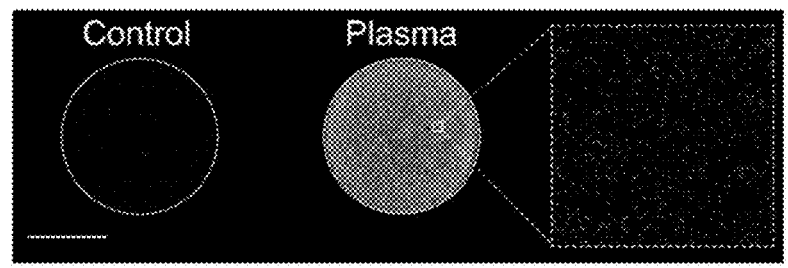
FIG. 2B shows the results of detecting t-tau present on the surface of plasma EV.
Figure 2C:
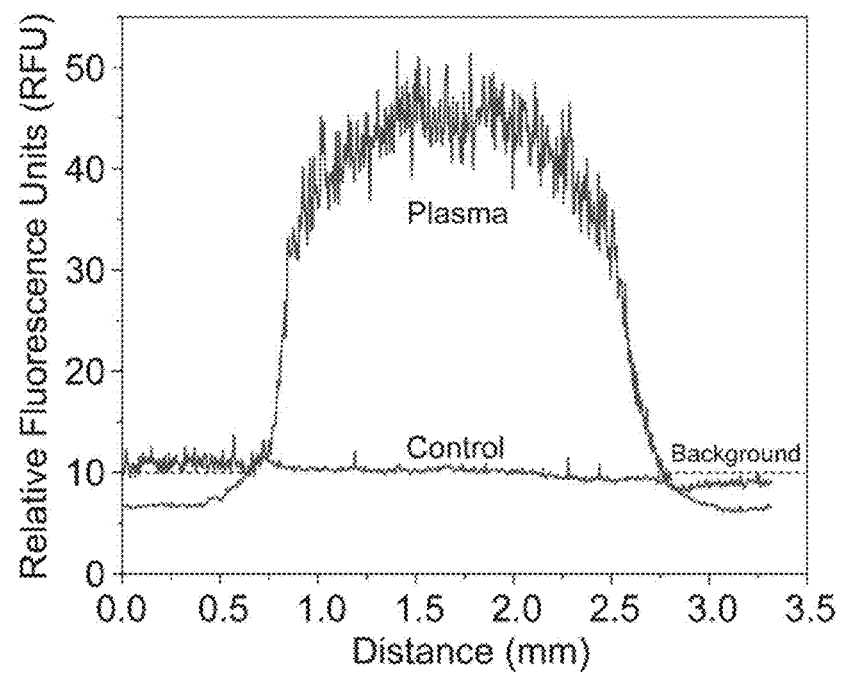
FIG. 2C shows the comparison of fluorescent signal of detecting t-tau present on the surface of EV between plasma sample and negative control.

In some embodiments, the disease to be diagnosed is Alzheimer's disease. Accordingly, the disease-specific antigen is an AD biomarker, such as a biomarker selected from the group consisting of t-tau, p-tau181, p-tau217, Aβ40, and Aβ42. In one example, the detection antibody is an anti-t-Tau antibody, and the capture antibody is an anti-CD81 antibody. Referring to FIG. 2B, much stronger signals were observed in plasma sample with EVs (right spot) when using anti-CD81 antibody as capture antibody for detection of t-Tau (total tau) protein on EV, compared to the negative control (isotype control, left spot). In some embodiments, this method can detect single EVs when sample is properly diluted (zoom-in region of FIG. 2B). The method of quantifying the fluorescent intensity of one whole spot can be known in the art, e.g., using python's scikit-image or commercialized software for microarray scanner. In some embodiments, the fluorescent intensity of the whole spot is quantified from its signal intensity distribution by measuring area between the curve and the background, as illustrated in FIG. 2C.

In some embodiments, the disease to be diagnosed is tumor or cancer. Accordingly, the disease-specific antigen is a tumor or cancer biomarker, such as a biomarker selected from the group consisting of CA 15-3, CA 125, CEA, HER2, EGFR, PSMA, EpCAM, and VEGF.

It is also understood that the emission spectrum of the detectable label linked to the control antibody should be different from that of the detection antibody, thus the source of the signals could be distinguished. In some embodiments, the detectable label is a fluorophore. In some embodiments, a fluorophore conjugated by the control antibody is Cy5, and a fluorophore conjugated by the control antibody is Cy3, or vice versa.

In some embodiments, the diagnosis method is based on the detection of multiple disease-specific antigens. In one embodiment, the method comprises: incubating a sample of the subject with a first detection antibody linked to a first detectable label and a second detection antibody linked to a second detectable label, wherein the sample comprises a circulating extracellular vesicle (EV), wherein the first detection antibody and the second detection antibody specifically bind to a first disease-specific antigen and a second disease-specific antigen present on the surface of the circulating EV respectively; contacting the sample with a capture antibody immobilized on a substrate, wherein the capture antibody specifically binds to a surface antigen of the circulating EV, thus immobilizing the circulating EV on the substrate; and detecting the first detectable label and the second detectable label on the circulating EV immobilized on the substrate, wherein the presence or abundance of the first detectable label and the second detectable label indicates a likelihood of the disease in the subject.

Figure 5:
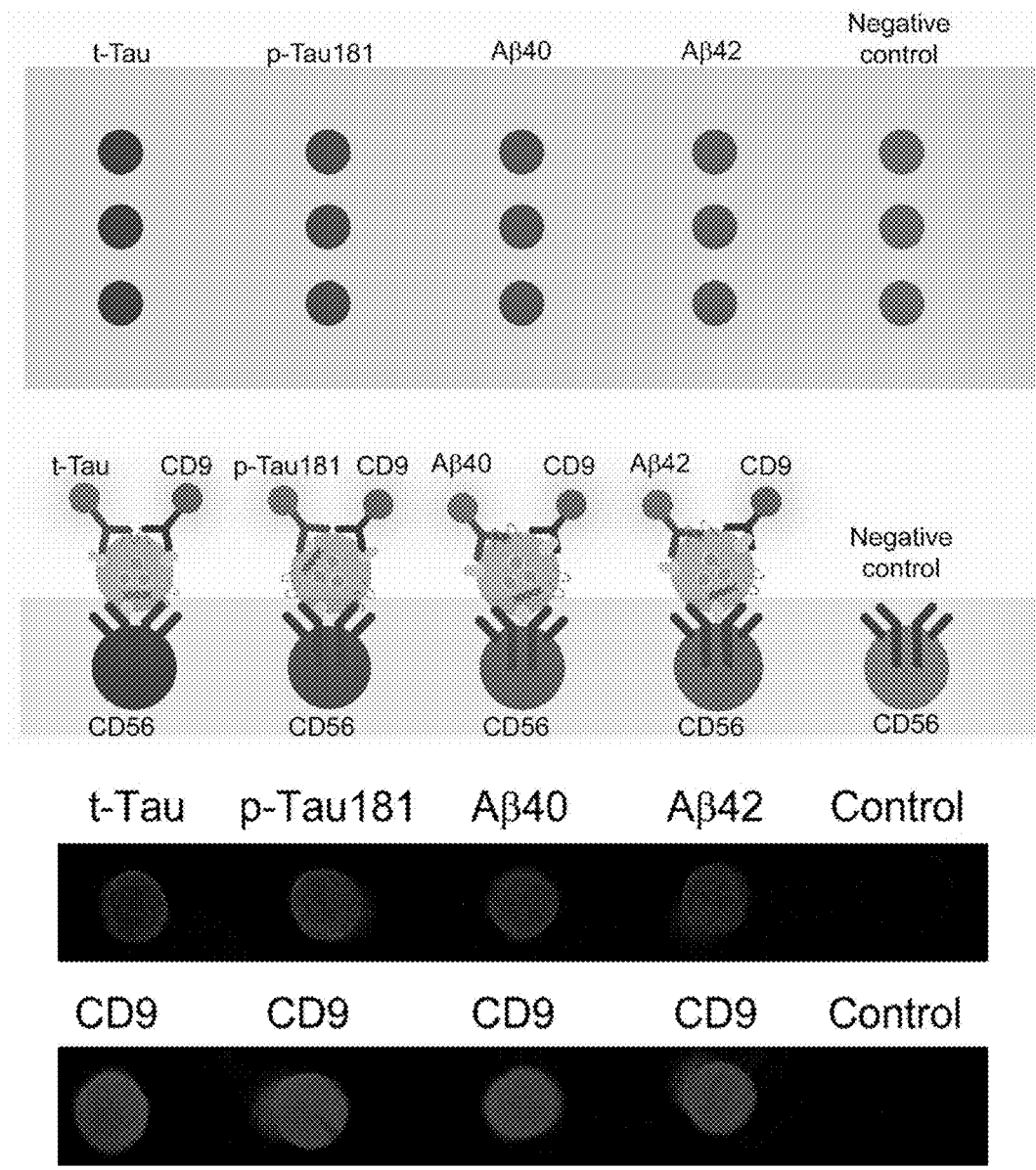
FIG. 5 shows the method and results for detecting five plasma EV surface proteins (p-Tau181, t-Tau, Aβ40, Aβ42, and CD9) for AD diagnosis.

In some embodiments, the method disclosed herein is used to diagnose Alzheimer's disease. As illustrated in FIG. 5, in one embodiment, the first and the second disease-specific antigen is selected respectively from the group consisting of t-tau, p-tau181, Aβ40, and Aβ42.

In some embodiments, the abundance of the first and the second detectable label is normalized with abundance of a control antigen present on the surface of the circulating EV. As illustrated in FIG. 5, in some embodiments, the control antigen is CD9.

Figure 6:
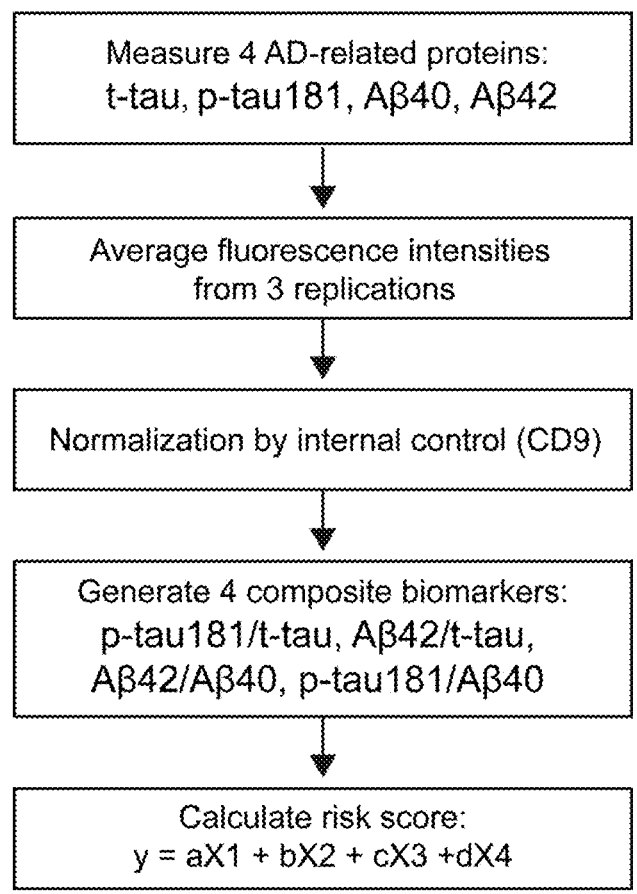
FIG. 6 shows the flow chart of generating a risk score for AD diagnosis based on the measurements of five plasma EV surface proteins (p-Tau181, t-Tau, Aβ40, Aβ42, and CD9).

The major steps of an exemplary method for diagnosing AD in a subject are illustrated in FIG. 6. Referring to FIG. 6, the first step is to measure the disease-specific antigens p-Tau181, t-Tau, Aβ40, and Aβ42 through antibodies specifically binds to p-Tau181, t-Tau, Aβ40, and Aβ42 respectively. Then, the final intensity for each detection antibodies is obtained from the average value of three replications. The measurement is considered valid when its intensity is at least 3-fold higher than the negative control. To reduce sample-to-sample variations and operation variations, the fluorescent intensity for each spot was normalized by dividing the fluorescent intensities of four disease-specific antigens, p-Tau181, t-Tau, Aβ40, and Aβ42, with the fluorescent intensities of common EV surface protein, CD9.

Then 4 composite biomarkers are obtained from the ratio of p-Tau181 to t-Tau, p-Tau181 to Aβ40, Aβ42 to Aβ40, and Aβ42 to t-Tau. Eventually, the risk score is calculated from the sum of each composite biomarker multiplied with their coefficients (FIG. 6). The coefficients of four composite biomarkers are obtained by a machine leaning algorithm based on the testing results from a group of AD patients and healthy controls.

As used herein, "machine learning" refers to a computer-implemented technique that gives computer systems the ability to progressively improve performance on a specific task with data, i.e., to learn from the data, without being explicitly programmed. Machine learning technique adopts algorithms that can learn from and make prediction on data through building a model, i.e., a description of a system using mathematical concepts, from sample inputs. A core objective of machine learning is to generalize from the experience, i.e., to perform accurately on new data after having experienced a learning data set. In the context of biomedical diagnosis or prognosis, machine learning techniques generally involves supervised learning process, in which the computer is presented with example inputs (e.g., signature of gene expression) and their desired outputs (e.g., responsiveness) to learn a general rule that maps inputs to outputs. Different models, i.e., hypothesis, can be employed in the generalization process. For the best performance in the generalization, the complexity of the hypothesis should match the complexity of the function underlying the data.

In some embodiments, the machine learning algorithm used herein is a support-vector machine (SVM). A Support Vector Machine (SVM) is a supervised classification technique that, at the most fundamental level, find a hyperplane or a boundary between two classes of data that maximizes the margin between the two classes. There are many planes that can separate the two classes, but only one plane can maximize the margin or distance between the classes.

Diagnostic Kit

In another aspect, the present disclosure provides a kit for diagnosing a disease in a subject. In some embodiments, the kit comprises: a detection antibody linked to a detectable label, wherein the detection antibody specifically binds to a disease-specific antigen present on the surface of a circulating EV; and a capture antibody, wherein the capture antibody specifically binds to a surface antigen of the circulating EV.

In some embodiments, the surface antigen is selected from the group consisting of CD9, CD18, CD63, CD81, CD56 and CD171.

In some embodiments, the disease-specific antigen is selected from the group consisting of t-tau, p-tau181, p-tau217, Aβ40, and Aβ42.

In some embodiments, the kit further comprises a substrate. In some embodiments, the substrate is a slide. In some embodiments, the slide is a glass slide. In some embodiments, the glass slide is coated with epoxy.

In some embodiments, the kit disclosed herein includes antibodies detecting multiple disease-specific antigens. In one example, the kit comprises: a first detection antibody linked to a first detectable label and a second detection antibody linked to a second detectable label, wherein the first detection antibody and the second detection antibody specifically binds to a first disease-specific antigen and a second disease-specific antigen present on the surface of a circulating EV respectively; and a capture antibody, wherein the capture antibody specifically binds to a surface antigen of the circulating EV.

In some embodiments, the first and the second disease-specific antigen is selected respectively from the group consisting of t-tau, p-tau181, p-tau217, Aβ40, and Aβ42.

Method of Treatment

In yet another aspect, the present disclosure provides a method for treating disease in a subject. In some embodiments, the method comprises administering to the subject a therapeutically effective amount of a drug useful for treating the disease, wherein the subject has been determined to have the disease by the diagnosing method disclosed herein. In some embodiments, the method comprises: i) diagnosis-incubating a sample of the subject with a detection antibody linked to a detectable label, wherein the sample comprises a circulating extracellular vesicle (EV), wherein the detection antibody specifically binds to a disease-specific antigen present on the surface of the circulating EV; contacting the sample with a capture antibody immobilized on a substrate, wherein the capture antibody specifically binds to a surface antigen of the circulating EV, thus immobilizing the circulating EV on the substrate; and detecting the detectable label on the circulating EV immobilized on the substrate, wherein the presence or abundance of the detectable label indicates a likelihood of the disease in the subject; ii) treatment; such as administering to the subject a therapeutically effective amount of a drug useful for treating the disease, wherein the subject has been determined to have the disease by the diagnosing method disclosed herein.

The drug that can be used in the method disclosed herein include, without limitation: alkylating agents or agents with an alkylating action, such as cyclophosphamide (CTX; e.g. Cytoxan®), chlorambucil (CHL; e.g. Leukeran®), cisplatin (CisP; e.g. Platinol®) busulfan (e.g. Myleran®), melphalan, carmustine (BCNU), streptozotocin, triethylenemelamine (TEM), mitomycin C, and the like; anti-metabolites, such as methotrexate (MTX), etoposide (VP16; e.g. Vepesid®), 6-mercaptopurine (6MP), 6-thioguanine (6TG), cytarabine (Ara-C), 5-fluorouracil (5-FU), capecitabine (e.g. Xeloda®), dacarbazine (DTIC), and the like; antibiotics, such as actinomycin D, doxorubicin (DXR; e.g. Adriamycin®), daunorubicin (daunomycin), bleomycin, mithramycin and the like; alkaloids, such as vinca alkaloids such as vincristine (VCR), vinblastine, and the like; and other antitumor agents, such as paclitaxel (e.g. Taxol®) and pactitaxel derivatives, the cytostatic agents, glucocorticoids such as dexamethasone (DEX; e.g. Decadron®) and corticosteroids such as prednisone, nucleoside enzyme inhibitors such as hydroxyurea, amino acid depleting enzymes such as asparaginase, leucovorin, folinic acid, raltitrexed, and other folic acid derivatives, and similar, diverse antitumor agents. The following agents may also be used as additional agents: amifostine (e.g. Ethyol®), dactinomycin, mechlorethamine (nitrogen mustard), streptozocin, cyclophosphamide, lornustine (CCNU), doxorubicin lipo (e.g. Doxil®), gemcitabine (e.g. Gemzar®), daunorubicin lipo (e.g. Daunoxome®), procarbazine, mitomycin, docetaxel (e.g. Taxotere®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon alpha, interferon beta, mitoxantrone, topotecan, leuprolide, megestrol, melphalan, mercaptopurine, plicamycin, mitotane, pegaspargase, pentostatin, pipobroman, plicamycin, teniposide, testolactone, thioguanine, thiotepa, uracil mustard, vinorelbine, and chlorambucil.

In some embodiment, the drug is a modulator of immune checkpoint. As used herein, the term "immune checkpoint" or "cancer immune checkpoint" refers to a molecule in the immune system that either turns up a signal (i.e., co-stimulatory molecules) or turns down a signal (i.e., inhibitory molecule) of an immune response. In certain embodiments, the immune checkpoint is selected from the group consisting of PD-1, PD-L1, PD-L2, LAG-3, TIM-1, CTLA-4, VISTA, B7-H2, B7-H3, B7-H4, B7-H6, 284, ICOS, HVEM, CD160, gp49B, PIR-B, KIR family receptors, TIM-1, TIM-4, BTLA, SIRPalpha (CD47), CD48, 284 (CD244), B7.1, B7.2, ILT-2, ILT-4, TIGIT and A2aR.

In certain embodiments, the drug is an immunomodulator. In the present invention, the term "immunomodulator" means a substance that alters the immune response by augmenting or reducing the ability of the immune system to produce antibodies or sensitize cells that recognize and react with the antigen that initiated their production. Immunomodulators may be recombinant, synthetic, or natural preparations and include cytokines, corticosteroids, cytotoxic agents, thymosin, and immunoglobulins. Some immunomodulators are naturally present in the body, and certain of these are available in pharmacologic preparations. In certain embodiments, immunomodulators are modulators of an immune checkpoint. Examples of immunomodulators include, but are not limited to, granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

In certain embodiments, the drug is an anti-hormonal agent. As used herein, the term "anti-hormonal agent" includes natural or synthetic organic or peptide compounds that act to regulate or inhibit hormone action on tumors.

In certain embodiments, the drug is a cytotoxic agent. Cytotoxic agents according to the present invention include DNA damaging agents, antimetabolites, anti-microtubule agents, antibiotic agents, etc.

In certain embodiments, the drug is an angiogenesis inhibitor. As used herein, an "anti-angiogenesis agent" means a substance that reduces or inhibits the growth of new blood vessels, such as, e.g., an inhibitor of vascular endothelial growth factor (VEGF) and an inhibitor of endothelial cell migration.

The drug described herein may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the drug may be administered in conjunction with other treatments.

A suitable, non-limiting example of a dosage of the drug is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. In some embodiments, the dosage of the drug in human is about 400 mg/day given every 12 hours. In some embodiments, the dosage of the drug in human ranges 300-500 mg/day, 100-600 mg/day or 25-1000 mg/day. The effective dose of drug disclosed herein may be administered as two, three, four, five, six or more sub-doses, administered separately at appropriate intervals throughout the day.

In some embodiments, the disease is Alzheimer's disease (AD). In some embodiments, the drug that can be used in treating AD includes, without limitation: antibodies targeting Aβ (such as Aduhelm), neuroprotective agents (such as ApoE2, Trem2, MT1G, or combinations thereof), hematopoietic stem progenitor cells expressing at least one neuroprotective agent (such as ApoE2, Trem2 or a metallothionein), antibody complex (such as antibody complex modified by a targeted functional molecule), drugs (such as polysaccharide) that inhibit the aggregation of AD-related proteins, like Aβ 42, compounds that degrade AD-related proteins, like microtubule-associated protein tau, NMDA receptor antagonists (such as Memantine), Acetylcholinesterase inhibitor (AChEI) (such as Tacrine, Donepezil, Galanthamine or Rivastigmine).

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLE

The present example illustrates the method for diagnosing AD.

Immobilization of Capture Antibodies

PBS-diluted antibodies (10 µg/mL) were spotted onto epoxy coated glass slides via a pipetting robot, followed by incubation at room temperature for 30 min to generate epoxy-amino groups between glass surface and antibodies. Thus, the capture antibodies were covalently immobilized on the glass slide.

Bind of Fluorescently Labeled Detection Antibodies to EVs

Plasma sample was diluted with the same volume of PBST buffer (1×PBS with 0.02% Tween-20) and incubated with fluorescently labeled detection antibodies (0.5 µg/mL) in a tube for 30 min at 37° C. After that, the sample was precisely spotted (1 µL/spot) onto the locations immobilized with capture antibodies on the slide via a pipetting robot, followed by incubation at room temperature for another 30 min in a humidity chamber.

Detection of Labels

After washed with PBST (0.05%) to remove unconjugated EVs and antibodies, the slide was scanned with a laser-induced fluorescence scanner to detect fluorescent signal from the detection antibodies.

This whole process takes around 1 h and does not require EV purification, available for rapid and sensitive detection and quantification of EV surface antigens.

Results

Figure 3:
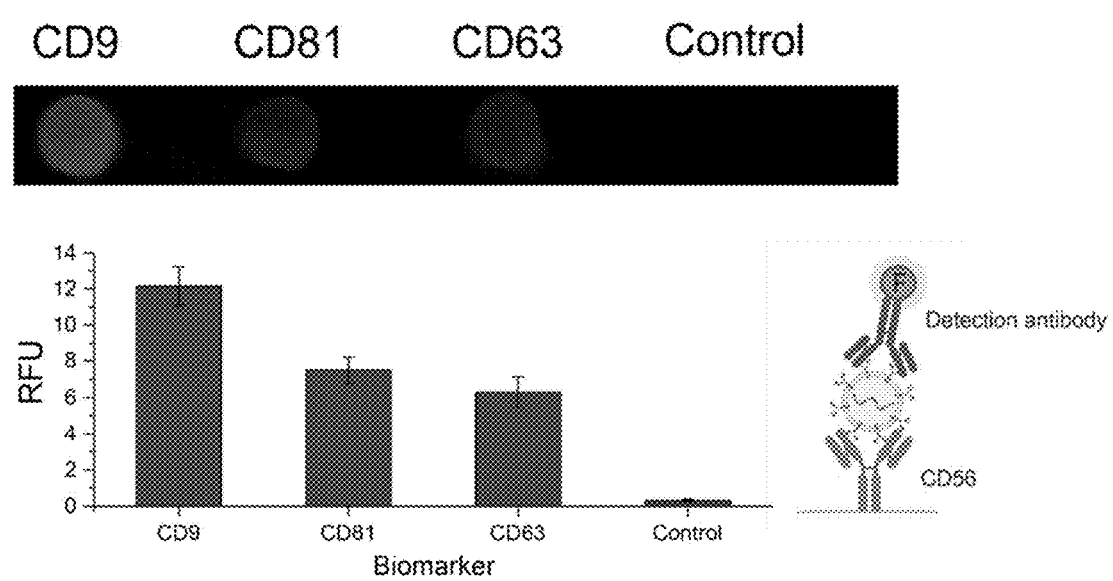
FIG. 3 shows the detection and quantification of biomarkers CD9, CD81, and CD63 present on the surface of plasma EV.
Figure 4:
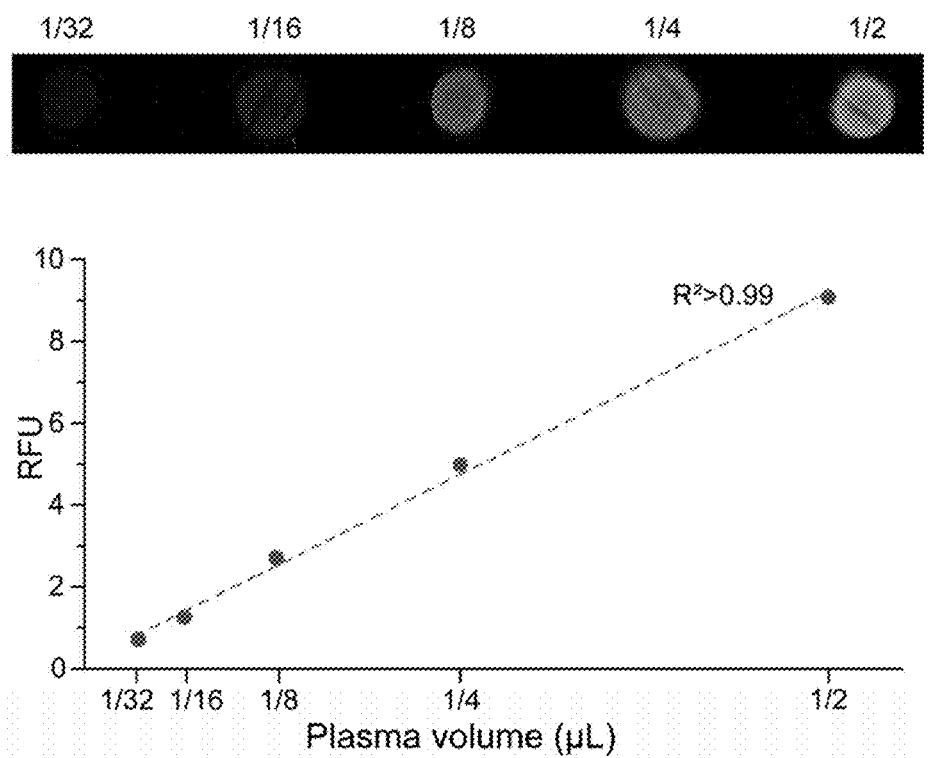
FIG. 4 shows the detection and quantification of biomarkers present on the surface of EVs from serially diluted plasma samples.

As shown in FIG. 3, detection of the biomarkers of CD9, CD81, and CD63 was performed using anti-CD56 antibody as a capture antibody, wherein CD56 is the neural cell adhesion molecule (NCAM). All the three markers could be detected with strongest signals from CD9. By serially diluting 1 µL plasma sample from 2 folds to 32 folds, the fluorescent signal from anti-CD9 detection antibody continuously decreased with a good linearity as shown in FIG. 4, indicating that this method can precisely quantify EV surface proteins.

FIG. 5 shows the application of this EV-based immunofluorescence assay for detection of five plasma EV surface proteins (p-Tau181, t-Tau, Aβ40, Aβ42, and CD9) for AD diagnosis. Using CD56 or CD171 as capture antibody, five arrays were generated on a glass slide with three spots (three replications) in each array. Each array was used to detect a different EV surface protein (p-Tau181, t-Tau, A040, and Aβ42) with a negative control (isotype control). CD9, the common biomarker on EVs, was detected in all spots, which was used as an endogenous control for normalization. Four aliquots of plasma samples were diluted with 1 volume of PBST (0.02% Tween-20) and incubated with respective Cy3 (555/570 nm) conjugated detection antibodies (p-Tau181, t-Tau, A040, and Aβ42), and Cy5 (650/670 nm) conjugated CD9 detection antibody at 37° C. for 30 min. After that, the samples were precisely spotted (1 µL/spot) onto the array dots with CD56 or CD171 capture antibody on the slide via a pipetting robot, followed by incubation at room temperature for another 30 min in a humidity chamber. After washed with PBST (0.05%) to remove unconjugated EVs and antibodies, the slide was scanned with two wavelengths (532 and 640 nm) via a laser-induced fluorescence scanner, such as Agilent SureScan microarray scanner or GenePix Microarray Scanner, to detect fluorescent signal from detection antibodies.

To calculate the fluorescence intensity of each spot, the scanned images of two wavelengths were imported into ImageJ software for analysis. The distribution of fluorescence intensity for each spot was then imported into Origin software to measure the area between the curve and the background, which was considered as the spot intensity.

Figure 7:
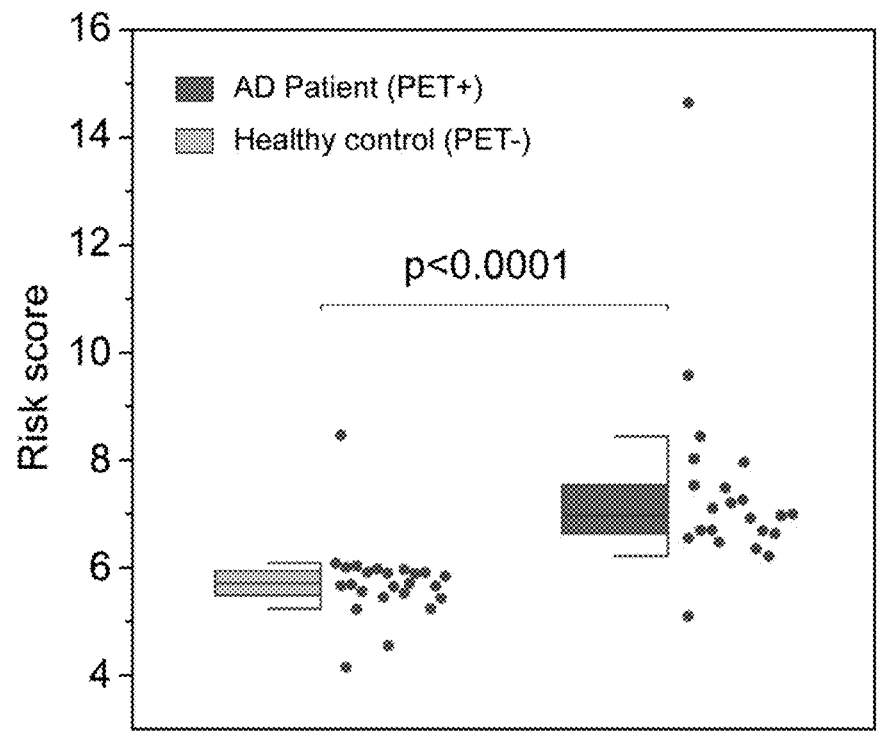
FIG. 7 shows the comparison of risk scores from 22 AD patients and 24 healthy controls.
Figure 8:
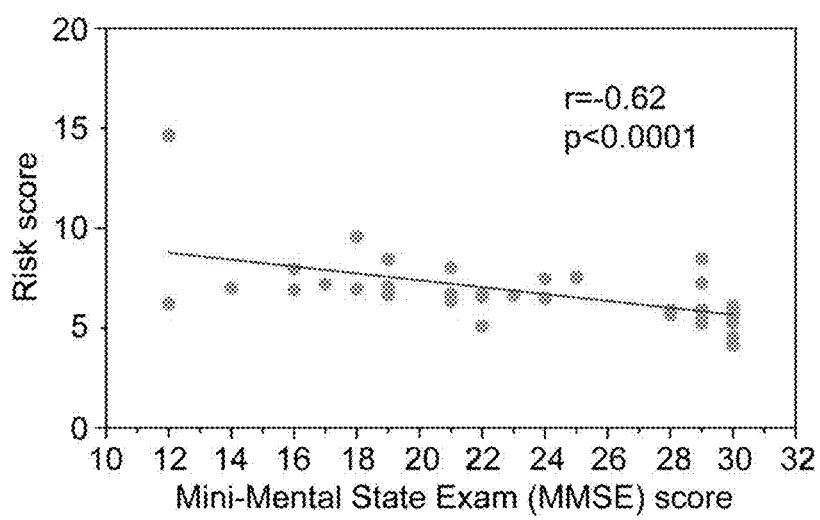
FIG. 8 shows the correlation between the risk score and MMSE (mini-mental state exam) score.

46 clinical plasma samples (AD patients: 22, healthy control: 24) were tested with this detection method and prediction model. Most of AD patients (amyloid PET positive) showed significantly higher values of risk scores (P<0.0001) compared to the healthy controls (amyloid PET negative) (FIG. 7), indicating that the risk score derived from the 4 composite biomarkers can be used for AD detection and screening by measuring the five proteins on individual's plasma EVs. The risk scores from clinical samples also showed strong correlation with the mini-mental state exam (MMSE) score (FIG. 8), in which a score of 20 to 24 suggested mild dementia, 13 to 20 suggested moderate dementia, and less than 12 indicated severe dementia.

Figure 9:
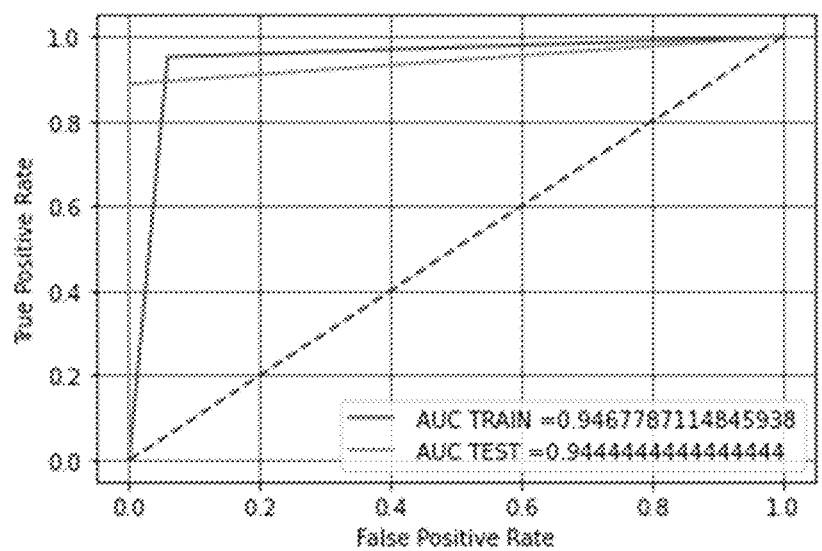
FIG. 9 shows the receiver operating characteristic (ROC) curve of the prediction model when the risk score is used as a predictor.

To evaluate the capability of this detection method and prediction model to discriminate AD patients from healthy controls, we further conducted receiver operator characteristic (ROC) analysis (FIG. 9). By employing the risk score as predictors, we have successfully discriminated AD patients and healthy controls with a sensitivity more than 90%, a specificity more than 90%, and an accuracy of nearly 95% for both training set and testing set.

What is claimed is:

1. A method comprising:
   (a) incubating a plasma sample of a subject with a panel of detection antibodies, respectively, wherein the panel of detection antibodies comprises an anti-t-tau antibody, an anti-p-tau181 antibody, an anti-Aβ40 antibody, and an anti-Aβ42 antibody;
   (b) allowing the panel of detection antibodies to specifically binds to circulating extracellular vesicles (EVs) in the plasma sample;
   (c) contacting the plasma sample from step (b) with an anti-CD56 antibody immobilized on a substrate, thus immobilizing the circulating EVs on the substrate;
   (d) detecting the panel of detection antibodies specifically bound to the circulating EVs immobilized on the substrate;
   (e) generating from the panel of detection antibodies detected in step (d) a panel of antibody ratios comprising a ratio of the anti-p-Tau181 antibody to the anti-t-Tau antibody, a ratio of the anti-p-Tau181 antibody to the anti-Aβ40 antibody, a ratio of the anti-Aβ42 antibody to the anti-Aβ40 antibody, and a ratio of the anti-Aβ42 antibody to the anti-t-Tau antibody; and (f) generating a risk score of Alzheimer's disease (AD) which is the sum of the panel of antibody ratios with coefficient thereof.

2. The method of claim 1, wherein the substrate is a glass slide.

3. The method of claim 2, wherein the glass slide is coated with epoxy.

4. The method of claim 3, wherein the anti-CD56 antibody is immobilized on the glass slide by micro-spotting.

5. The method of claim 1, wherein each of the panel of detection antibodies is linked to a fluorophore or a fluorescent microsphere.

6. The method of claim 5, wherein the panel of detection antibodies is detected through a laser-induced confocal fluorescence scanner or a fluorescence microscope.

7. The method of claim 1, further comprising
incubating the sample with a control antibody specifically binds to a control antigen present on the surface of the circulating EVs; and
detecting the control antibody specifically bound to the circulating EVs immobilized on the substrate.

8. The method of claim 7, wherein the control antigen is selected from the group consisting of CD9, CD63, and CD81.

9. The method of claim 7, further comprising normalizing the abundance of each of the panel of detection antibodies specifically bound to the circulating EVs immobilized on the substrate with the abundance of the control antibody specifically bound to the circulating EVs immobilized on the substrate.

10. The method of claim 1, wherein the coefficient is determined by using a machine learning algorithm to study a training data set.

11. The method of claim 10, wherein the machine learning algorithm is support vector machine (SVM).

12. The method of claim 1, further comprising administering to the subject a drug treating AD selected from the group consisting of an antibody targeting Aβ, a neuroprotective agent, a hematopoietic stem progenitor cell expressing at least one neuroprotective agent, a drug that inhibits the aggregation of Aβ 42, a compound that degrade microtubule-associated protein tau, a NMDA receptor antagonist, and an Acetylcholinesterase inhibitor.

* * * * *